United States Patent [19]
Ide et al.

[11] Patent Number: 5,599,783
[45] Date of Patent: Feb. 4, 1997

[54] CLEANING SOLVENT COMPOSITION AND A METHOD FOR CLEANING OR DRYING ARTICLES

[75] Inventors: Satoshi Ide; Takahiro Matsuda; Hirokazu Aoyama; Akinori Yamamoto, all of Settsu, Japan

[73] Assignee: Daikin Industries, Ltd., Osaka, Japan

[21] Appl. No.: 416,750

[22] PCT Filed: Aug. 12, 1994

[86] PCT No.: PCT/JP94/01347

§ 371 Date: May 9, 1995

§ 102(e) Date: May 9, 1994

[87] PCT Pub. No.: WO95/05448

PCT Pub. Date: Feb. 23, 1995

[30] Foreign Application Priority Data

Aug. 16, 1993 [JP] Japan .................. 4-222781

[51] Int. Cl.$^6$ .................. C11D 7/50; C11D 7/30; B08B 3/08; C23G 5/028
[52] U.S. Cl. .................. 510/412; 510/365; 510/364; 510/273; 510/175; 134/26; 134/40; 134/42
[58] Field of Search .................. 252/170, 171, 252/172, 194, 364, DIG. 9; 134/40, 42, 26; 510/365, 364, 412, 273, 175

[56] References Cited

U.S. PATENT DOCUMENTS

| | | | |
|---|---|---|---|
| 3,850,759 | 11/1974 | Hutchinson | 203/58 |
| 3,903,012 | 9/1975 | Brandreth | 252/194 |
| 4,559,154 | 12/1985 | Powell | 252/69 |
| 5,176,757 | 1/1993 | Anton | 134/42 |
| 5,268,122 | 12/1993 | Rao et al. | 252/171 |
| 5,346,645 | 9/1994 | Omure et al. | 252/194 |

FOREIGN PATENT DOCUMENTS

| | | |
|---|---|---|
| 4-25598 | 1/1992 | Japan . |
| 5-78652 | 3/1993 | Japan . |
| 5-184807 | 7/1993 | Japan . |
| 5-331489 | 12/1993 | Japan . |
| 5-331490 | 12/1993 | Japan . |
| 6-007606 | 1/1994 | Japan . |
| 6-271490 | 7/1994 | Japan . |
| 6-271489 | 9/1994 | Japan . |
| 6-271488 | 9/1994 | Japan . |
| 6-271491 | 9/1994 | Japan . |

OTHER PUBLICATIONS

Fuller et al, "Some Isomeric Hexafluorocyclobutanes and Pentafluorocyclobutenes", *J. Chem. Soc.* 1961 pp. 3198–3203.

Heitzman et al, "Fluororcyclopentanes Part I. The 1H, 2H– and 1H, 3H–octafluorocyclopentanes, and 1H,3H/2H–Heptafluorocyclopentane", *J. Chem. Soc.* 1963 pp. 281–289.

Burdon et al, "Fluorocyclopentanes, Part III. The Isomeric 1H:2H:3H– and 1H:2H:4H–Heptaflurorcyclopentanes and the 1H:2H:3H:4H–Hexafluorocyclopentanes", *J. Chem. Soc.* Mar. 1965 pp. 2382–2391.

Van Der Puy, Michael, et al., "Estimation of hydrocarbon solubilities in hydrofluorocarbons", Journal of Fluorine Chemistry, 67(3), 215–224 Jun. 1994.

Primary Examiner—Douglas J. McGinty
Attorney, Agent, or Firm—Larson & Taylor

[57] ABSTRACT

A cleaning solvent composition comprising at least one selected from the group consisting of 1H,2H/-hexafluoro-cyclobutane, 1,2,2,3,3-pentafluoro-cyclobutane, 1,2,2,3,3,4,4,5,5-nonafluorocyclopentane, 1H/2H-octafluorocyclopentane, 1H,2H/-octafluorocyclopentane, 1H/3H-octafluorocyclopentane, 1H,4H,2H/-heptafluorocyclopentane, 1H,2H/4H-heptafluorocyclopentane, 1H,2H,4H/-heptafluorocyclopentane, 1H,3H/2H-heptafluorocyclopentane, 1H,2H/3H-heptafluorocyclopentane and 1H,2H/3H-heptafluorocyclopentane and a method for cleaning or drying acticles employing thereof and use of the composition as a cleaning agent.

4 Claims, No Drawings

CLEANING SOLVENT COMPOSITION AND A METHOD FOR CLEANING OR DRYING ARTICLES

TECHNICAL FIELD

The present invention relates to a cleaning solvent composition and a method for cleaning or drying acticles, for example, relates to a cleaning solvent composition suitable for removing flux, fats and oils, dust, etc., and a method for cleaning or drying acticles employing thereof.

BACKGROUND ART

When IC components, precision machinery components, etc. are produced, cleaning the components with organic solvent is usually performed heretofore to remove flux, dust, etc. adhered to the components in a process of assembly.

1,1,2-Trichloro-1,2,2-trifluoroethane (hereinafter referred to as R-113) is widely employed as the organic solvent. R-113 is nonflammable, low in toxicity in vivo and excellent in stability. In addition, R-113 has a moderate solubility so that R-113 selectively solubilizes a variety of dirt without attack on metals, plastics, elastomer, etc. When flux on printed-circuit board is cleaned, R-113 is particularly advantageous, because the cleaned articles are composite components made of metals, plastics, elastomer, etc., in most cases.

Since R-113 is suspected of destructing the ozonesphere, as a result, causing cutaneous cancer, utilization of R-113 is gradually controlled.

Cyclic fluorinated hydrocarbons such as 1,1,2,2,3,3-hexafluorocyclopentane disclosed in U.S. Pat. No. 5,176,757 and 1,1,2,2-tetrafluorocyclobutane disclosed in Japanese Unexamined Patent Publication No. 5-140594 are known in addition to R-113 as cleaning solvents.

Since the known cyclic compounds have a number of hydrogen atoms leading to flammability, the compounds may cause a trouble on safety as a cleaning agent when used at elevated temperature and recycled.

DISCLOSURE OF THE INVENTION

The inventors of the present invention, who were engaged in intensive research in view of the prior art, discovered that specific fluorohydrocarbons (1) have no possibility to deplete ozone because of lack of chlorine in the molecule; (2) exert an excellent effect on cleaning flux, fats and oils, dust, etc.; (3) have similarly moderate solubility as R-113 leading to selective solubilization and removal of a variety of dirt without attack on composite components made of metals, plastics, elastomer, etc.; (4) exert an excellent drying effect to remove water from articles by dissolving and separating water adhered to articles; and (5) are excellent as a rinsing agent employed in a cleaning process in a combination with organic solvents, and accomplish the invention.

Thus, the invention is a cleaning solvent composition comprising at least one selected from the group consisting of 1H,2H/-hexafluorocyclobutane, 1,2,2,3,3-pentafluorocyclobutane, 1,2,2,3,3,4,4,5,5-nonafluorocyclopentane, 1H/2H-octafluorocyclopentane, 1H,2H/-octafluorocyclopentane, 1H/3H-octafluorocyclopentane, 1H,4H,2H/-heptafluorocyclopentane, 1H,2H/4H-heptafluorocyclopentane, 1H,2H,4H/-heptafluorocyclopentane, 1H,3H/2H-heptafluorocyclopentane, 1H,2H/3H-heptafluorocyclopentane and 1H,2H/3H-heptafluorocyclopentane (hereinafter referred to as invention I). The invention is preferably a cleaning solvent composition comprising 1H,2H/-hexafluorocyclobutane.

According to the cleaning solvent composition of the invention, the above-mentioned cyclic fluorohydrocarbons, as an active ingredient, demonstrate performance (1) to (5), and is a very useful substance as substitute for R-113. Structural formula, physical properties and methods for producing thereof are shown below with original sources.

TABLE 1

| Structure | | b.p. | Synthesis Document |
|---|---|---|---|
| (cyclobutane with F, H, H) | 1H, 2H/ | 63° C. | J. Chem. Soc., 3198–3203(1961) |
| (cyclobutane with F, H, H, H) | | 50° C. | |
| (cyclopentane with F, H) | | 38.5° C. | J. Chem. Soc., 2382–2391(1965) J. Chem. Soc., 281–289(1963) |
| (cyclopentane with F, H, H) | 1H/2H 1H, 2H/ | 50° C. 78° C. | J. Chem. Soc., 2382–2391(1965) J. Chem. Soc., 281–289(1963) |
| (cyclopentane with F, H, H) | 1H/3H 1H, 3H/ | 58° C. 65° C. | J. Chem. Soc., 2382–2391(1965) J. Chem. Soc., 281–289(1963) |
| (cyclopentane with F, H, H, H) | 1H, 4H, 2H/ 1H, 2H/4H 1H, 2H, 4H | 78° C. 94° C. 115° C. | J. Chem. Soc., 2382–2391(1965) J. Chem. Soc., 281–289(1963) |
| (cyclopentane with F, H, H, H) | 1H, 3H/2H 1H, 2H/3H 1H, 2H, 3H/ | 65° C. 84° C. 135° C. | J. Chem. Soc., 2382–2391(1965) J. Chem. Soc., 281–289(1963) |

In the table, 1H, 2H/, etc. indicate difference of position of hydrogen atoms.

Further, the cyclic fluorohydrocarbons may have a trifluoromethyl group as a substituent. An example of preferable compounds having a substituent is 1-trifluoromethyl-1,2,2,4-tetrafluorocyclobutane.

The cyclic fluorohydrocarbons may be substituted by one or two trifluoromethyl groups, preferably substituted by one trifluoromethyl group.

Structural formula, physical property and a method for producing the compound are shown below with an original source.

TABLE 2

| | b.p. | Synthesis, Document |
|---|---|---|
| (cyclic structure with H, CF₃, F, H, H substituents) | 68° C. | DEP 2157397 |

In the invention I, content of said cyclic fluorohydrocarbons are not specifically limited to, but usually at least 70% by weight, preferably at least 80% by weight.

The cleaning solvent composition may contain at least one selected from organic solvent (I) such as hydrocarbons (I), alcohols (I), esters (I) and ketones (I) to improve solvency power thereof.

The amount of organic solvent (I) blended is not specifically limited to, but usually up to 30% by weight, preferably 2 to 10% by weight, more preferably 3 to 8% by weight based on the total amount of cleaning solvent composition.

When azeotropic compositions exist in a mixture of said cyclic fluorohydrocarbons and said organic solvents (I), the cleaning solvent composition is preferably employed at the azeotropic compositions.

Said hydrocarbons (I) are not specifically limited to, but preferably hexane, heptane, isoheptane, octane, isooctane, methylcyclopentane, cyclohexane, methylcyclohexane, toluene, etc.

Said alcohols (I) are not specifically limited to, but preferably chain saturated alcohols having 1–6 carbon atoms, such as methanol, ethanol, n-propanol, isopropanol, n-butyl alcohol, sec-butyl alcohol, tert-butyl alcohol, pentyl alcohol, sec-amyl alcohol, 1-ethyl-1-propanol, 2-methyl-1-butanol, isopentyl alcohol, tert-pentyl alcohol, 3-methyl-2-butanol, neopentyl alcohol, 2-ethyl-1-butanol. Methanol, ethanol, isopropanol, n-propanol, etc. are especially preferable.

Said esters (I) are not specifically limited to, but preferably esters composed of fatty acid having about 1–5 carbon atoms and lower alcohols having about 1–6 carbon atoms. Examples of esters (I) are methyl acetate, ethyl acetate, propyl acetate, isopropyl acetate, butyl acetate, isobutyl acetate, pentyl acetate, hexyl acetate, methyl propionate, ethyl propionate, propyl propionate, isopropyl propionate, methyl butyrate, ethyl butyrate, methyl valerate, etc. Methyl acetate, ethyl acetate, propyl acetate and butyl acetate are particularly preferable.

Said ketones (I) are not specifically limited to, but preferably compounds represented by the formula R—CO—R' wherein R and R' demonstrate straight or branched saturated hydrocarbon group having 1–4 carbon atoms. Examples of ketones (I) are acetone, 2-butanone, 2-pentanone, 3-pentanone, 4-methyl-2-pentanone, etc. Acetone, 2-butanone and 4-methyl-2-pentanone are particularly preferable.

The cleaning solvent composition of the invention may further contain ingredients conventionally blended in this type of cleaning solvent according to each of objects. The ingredients include cleaning auxiliaries and stabilizer such as surfactant, hydrogen-containing chlorofluorohydrocarbons having low possibility to deplete ozone, and hydrogen-containing fluorohydrocarbons having no possibility to deplete ozone.

The cleaning solvent composition of the invention is useful for cleaning articles to which pollutant is adhered, for example, useful for cleaning flux, grease, oil, wax and like fats and oils, and for removing dirt. The cleaning solvent composition of the invention is also useful for removing and drying water adhered to articles.

Examples of articles for cleaning are IC components, precision machinery components, etc., made of materials such as metals, plastics, elastomer, etc.

A conventional cleaning method may be applied to the former, when cleaning flux, fats and oils, and removing dirt. Specifically, wiping off by hand, dipping, spraying, rocking, ultrasonic cleaning, steam cleaning and like methods are exemplified.

A method for drying articles are conducted by contact with the cleaning solvent composition which dissolves and separates water in the latter case.

According to the invention, cleaning of articles may be conducted by a cleaning step to remove pollutant comprising putting pollutant-adhered articles in contact with solvents, other than the cleaning solvent composition of the invention, in particular, organic solvents (II) having a boiling point of 100° C. or more comprising at least one selected from aliphatic hydrocarbons (II), aromatic or alicyclic hydrocarbons (II), higher alcohols (II), ethers (II) and organic silicons (II); and a cleaning step comprising putting the above-treated articles in contact with the cleaning solvent composition of the invention (hereinafter referred to as invention II).

Examples of the organic solvents (II) having a boiling point of 100° C. or more are shown below.

Aliphatic hydrocarbons (II): n-hexane, isoheptane, isooctane, gasoline, petroleum naphtha, mineral spirit and kerosene.

Aromatic or alicyclic hydrocarbons (II): benzene, toluene, xylene, cyclohexane, methylcyclohexane, tetralin, decalin, dipentene, cymene, terpene, α-pinene and turpentine oil.

Higher alcohols (II): 2-ethylbuthylalcohol, 2-ethylhexylalcohol, nonylalcohol, decylalcohol and cyclohexanol.

Glycol ethers: ethyleneglycol monomethylether, ethyleneglycol monobutylether, diethyleneglycol monoethylether, diethyleneglycol dimethylether and diethyleneglycol dimethylether.

Organic silicons (II): dimethylpolysiloxane, cyclopolysiloxane and octamethylcyclotetrasiloxane.

The organic solvents (II) may optionally contain nonionic surface active agents and/or water In a rinsing step of said cleaning method, rinsing may be conducted by using a mixture comprising said cyclic fluorohydrocarbons and at least one rinsing auxiliary selected from the group consisting of hydrocarbons (III), lower alcohols (III) and ketones (III) shown below. A proportion of rinsing auxiliaries blended is preferably less than 20%. When the proportion of rinsing auxiliaries blended is less than 10%, the mixture becomes nonflammable, thereby more preferable.

As shown above, said rinsing auxiliaries and said cyclic fluorohydrocarbons may be blended. The mixture is more preferably azeotropic. A mixture comprising said cyclic fluorohydrocarbons and at least one rinsing auxiliary selected from the group consisting of hydrocarbons (III), lower alcohols (III) and ketones (III) is preferably azeotropic or azeotrope-like composition.

Examples of usable rinsing auxiliaries are shown below.

Hydrocarbons (III): n-pentane, n-hexane, isohexane, n-heptane, isooctane, cyclopentane, cyclohexane and methylcyclohexane.

Lower alcohols (III): methyl alcohol, ethyl alcohol, n-propyl alcohol, isopropyl alcohol and butyl alcohol.

Ketones (III): acetone and methylethylketone.

Said rinsing auxiliary has a boiling point of usually 100°–20° C., preferably 100°–30° C., because said rinsing auxiliary is capable of being employed in a steam rinsing step or recycled after fractionation. The rinsing auxiliaries having a similar boiling point of the cyclic fluorohydrocarbons blended or forming an azeotopic or azeotope-like composition within said range of boiling point are more preferable. In the latter case, a boiling point of said rinsing auxiliaries may be outside of said range of boiling point.

When a variety of pollutants are cleaned and removed by the cleaning method comprising a cleaning step and a rinsing step of the invention, articles to which pollutants are adhered are first brought into contact with said organic solvent (II).

The way of contact of articles with organic solvent (II) is not specifically limited to, but conducted by any method, such as a method of dipping articles into organic solvent, a method of spraying organic solvent on the articles, etc.

The temperature of organic solvent (II) during contact is not specifically limited to, but preferably heated in a small extent to accelerate removal of pollutants as long as the temperature is below flash point of organic solvent (II).

Ultrasonic vibration, agitation, brushing, and like means to impart mechanical force are combined with the treatment by dipping.

The articles and organic solvent (II) are contacted for a sufficient time to remove pollutants in a desired extent. Subsequently, the article cleaned by contact with organic solvent is rinsed by contact with rinsing fluid comprising cyclic fluorohydrocarbons. The method for contact of articles with rinsing fluid is not specifically limited to, but performed by a method of dipping articles into rinsing fluid, a method of cleaning articles by steam of rinsing fluid, etc.

To improve rinsing effect, rinsing may be conducted by repeating the same rinsing method, or combining different rinsing methods. In particular, cleaning effects are improved by combining dipping or spraying method and steam cleaning. In this case, steam rinsing process is preferably conducted after rinsing process.

The invention further relates to use of a composition as a cleaning agent comprising at least one selected from the group consisting of 1H,2H/-hexafluorocyclobutane, 1,2,2,3,3-pentafluorocyclobutane, 1,2,2,3,3,4,4,5,5-nonafluorocyclopentane, 1H/2H-octafluorocyclopentane, 1H,2H/-octafluorocyclopentane, 1H/3H-octafluorocyclopentane, 1H,4H,2H/-heptafluorocyclopentane, 1H,2H/4H-heptafluorocyclopentane, 1H,2H,4H/-heptafluorocyclopentane, 1H,3H/2H-heptafluorocyclopentane, 1H,2H/3H-heptafluorocyclopentane and 1H,2H/3H-heptafluorocyclopentane. The cleaning composition of the invention contains said special cyclic fluorohydrocarbons as an active ingredient so that the composition exerts excellent effects of (1) to (4) below.

(1) The composition is nonflammable and has no possibility to deplete ozone because of lack of chlorine atom in the molecule.
(2) The composition exerts excellent effects on cleaning flux, fats and oils, dirt, etc.
(3) The composition similarly has moderate solubility as R-113 leading to selective solubilization of a variety of pollutants without attack on composite components made of metals, plastics, elastomer, etc.
(4) The composition exerts excellent drying effects to remove water from articles by dissolving and separating water adhered to articles.

Further, the cleaning solvent composition exerts excellent effects of (1) to (4) below when employed as a rinsing agent.
(i) Cleaning and rinsing fluid do not cause any environmental problem such as environmental pollution or ozone depletion because of lack of chlorine atom.
(ii) No water is employed in a steps of cleaning and rinsing leading to simplification of a step and facilities. Specifically, purification treatment of water and treanment of waste water are not required, a variety of facilities, land and operating cost for said treatments are not needed. Further, a drying step, required when employing water, is not needed.
(iii) Rinsings employing nonflammable aliphatic fluorohydrocarbons has no risk of flaming and explosion while steam cleaning.
(iv) Substitution of cleaning and rinsing fluids for the organic solvents and said cyclic fluorohydrocarbons makes effect without large-scale remodeling of a conventional cleaning facilities in which chlorofluorohydrocarbons or chlorohydrocarbons are employed.
(v) Cleaning is sufficiently conducted by employing the organic solvents, and the organic solvents are sufficiently rinsed by cyclic fluorohydrocarbons without water. The cyclic fluorohydrocarbons may be recovered and recycled and is safe to cause no environmental destruction when released.

EXAMPLE

The invention is described in more detail using the examples. The present invention is in no way limited by the examples and may be modified in a variety of ways based on the technical ideas of the invention.

Example 1

<Degreasing Test>

Cylindrical wire sheets (25$\phi$×15$^H$ mm) of 100 mesh to which spindle oil was adhered were dipped in the following cleaning solvent compositions (Nos. 1–4) and ultrasonic cleaning was performed for 60 seconds. Steam cleaning was further performed for a degreasing and cleaning test. The amount of residual oil on the wire sheets was determined with oil content meter (product of HORIBA LIMITED) to calculate a proportion of removed oil as cleaning ratio. The results are shown in table 3 below. Table 3 clearly demonstrates that all wire sheets were sufficiently cleaned.

TABLE 3

| | Cleaning Solvent Composition | | |
|---|---|---|---|
| No. | Cyclic fluorohydrocarbon | Proportion (%) | Cleaning ratio (%) |
| 1 | 1H,2H/-hexafluorocyclobutane | 100 | 99.7 |
| 2 | 1H/2H-octafluorocyclopentane | 100 | 99.7 |
| 3 | 1H,2H/-hexafluorocyclobutane/ n-heptane | 90/10 | 99.9 |
| 4 | 1H/2H-octafluorocyclopentane/ cyclohexane | 90/10 | 99.9 |

Example 2

Iron test pieces (30×30×2' mm, 7$\phi$ hole in the center) were dipped in water, subsequently dipped in the solvent compositions (Nos.5–8) of the invention at room temperature for 30 seconds, and then washed with a predetermined amount of dry methanol. Water content of the wash liquid (methanol) was determined by Karl Fischer method to calculate a ratio of removed moisture. The results are shown in table 4 below. Table 4 shows that in all cases removal of moisture (hydro-extraction) is sufficient enough.

TABLE 4

| No. | Cleaning Solvent Composition | | Ratio of removed moisture (%) |
|---|---|---|---|
| | Cyclic fluorohydrocarbon | Proportion (%) | |
| 5 | 1H,1H,2H/-pentafluorocyclobutane | 100 | 95 |
| 6 | 1H/3H-octafluorocyclopentane | 100 | 95 |
| 7 | 1H,1H,2H/-pentafluorocyclobutane/ methanol | 95/5 | 99 |
| 8 | 1H/3H-octafluorocyclopentane/ ethanol | 95/5 | 99 |

Example 3

<Flammability test>

Flammability of the above-mentioned cleaning solvent compositions of the invention (Nos.1–8) was determined with Tada Closed-Type Flash Point Analyzer. As a results, the compounds or compositions of Nos.1–8 has no flammability. As comparative tests, flammability of 1,1,2,2,3,3-hexafluorocyclopentane and 1,1,2,2-tetrafluorocyclobutane were determined. The two compounds had flammability.

Example 4

<Material test>

A variety of plastics shown in table 5 below were dipped in the cleaning solvent compositions (Nos.1–8) of the invention at 25° C. for 10 minutes. Weight change of the plastics immediately after taken out was determined and evaluated according to the following criteria.
0: hardly affected (weight change 0–1%).
1: slightly swelled, but substantially no problem (weight change 1–5%).
2: the plastics were swelled and attacked (weight change 5% or more).

The results are shown in table 5. Table 5 shows that all plastics are not substantially attacked.

TABLE 5

| Cleaning Solvent Composition No. | ABS | Poly-carbonate | Acryl resin | Epoxy resin | Poly-phenylene oxide |
|---|---|---|---|---|---|
| 1 | 0 | 0 | 1 | 0 | 0 |
| 2 | 0 | 0 | 1 | 0 | 0 |
| 3 | 0 | 0 | 1 | 0 | 1 |
| 4 | 0 | 0 | 1 | 0 | 1 |
| 5 | 0 | 0 | 1 | 0 | 0 |
| 6 | 0 | 0 | 1 | 0 | 0 |
| 7 | 0 | 0 | 1 | 0 | 1 |
| 8 | 0 | 0 | 1 | 0 | 1 |

Example 5

<Removal of rosin flux>

Rosin flux (trade mark "H1-15" Asahi Chemical Research Laboratory Co., Ltd.) was jetted and coated on a printed-circuit boards (10 cm×10 cm). After preliminary drying, the boards were heated at 250° C. for 1 minute to prepare test pieces. The test pieces were cleaned and rinsed by dipping the test piece in the cleaning and rinsing fluids shown in table 6 under a variety of conditions. Said rinsing treatment was optionally combined. A conventional rinsing was performed as a comparative example. Appearance and an amount of ionic residue of the test pieces after cleaning and rinsing treatments are shown in table 7, as an effect to remove rosin flux. As shown in table 7, the method of the invention is effective enough to remove rosin flux. The amount of ionic residue was determined by OMEGA METER 600SMD (NIPPON ALPHA METALS CO., LTD.).

TABLE 6

| | | Cleaning | Rinsing | Steam rinsing |
|---|---|---|---|---|
| Example 5 | (1) | Ethyleneglycol monoethyl ester 40° C., 30 sec | 1H,2H/-hexafluorocyclobutane 25° C., 30 sec | The same as the left column 30 sec |
| | (2) | Terpene 60° C., 30 sec | 1H/2H-octafluorocyclopentane 25° C., 30 sec | The same as the left column 30 sec |
| Comparative Example 1 | (1) | Terpene 60° C., 30 sec | Terpene 60° C., 30 sec | None |
| | (2) | Terpene 60° C., 30 sec | Water 60° C., 30 sec | None |

TABLE 7

| | | Appearance | Ionic residue ($\mu$gNaCl/in$^2$) |
|---|---|---|---|
| Example 5 | (1) | Clean surface | 4.0 |
| | (2) | Clean surface | 5.5 |
| Comparative Example 1 | (1) | Not dried | 18.0 |
| | (2) | White residue | 25.0 |

We claim:

1. A cleaning solvent composition comprising 1H,2H/-hexafluorocyclobutane and at least one organic solvent selected from the group consisting of:

hydrocarbons consisting of hexane, heptane, isoheptane, octane, isooctane, methylcyclopentane, cyclohexane, methylcyclohexane and toluene; alcohols having 1–6 carbon atoms; esters composed of fatty acid having about 1–5 carbon atoms and lower alcohols having about 1–6 carbon atoms; and ketones represented by the formula R—CO—R$^1$ wherein R and R$^1$ represent straight or branched saturated hydrocarbons having 1–4 carbon atoms.

2. A method for cleaning articles comprising a cleaning step to remove pollutants comprising putting pollutant adhered articles in contact with at least one organic solvent having a boiling point of 100° C. or higher selected from the group consisting of aliphatic hydrocarbons consisting of n-hexane, isoheptane, isooctane, gasoline, petroleum naphtha, mineral spirit and kerosene; aromatic or alicyclic hydrocarbons consisting of benzene, toluene, xylene, cyclohexane, methylcyclohexane, tetralin, decalin, dipentene, cymene, terpene, α-pinene and turpentine oil; higher alcohols consisting of 2-ethylbutylalcohol, 2-ethylhexylalcohol, nonylalcohol, decylalcohol and cyclohexanol; glycol ethers consisting of ethyleneglycol monomethylether, ethyleneglycol monobutylether, diethyleneglycol monoethylether, diethyleneglycol dimethylether and diethyleneglycol monoethylether; and organic silicons consisting of dimethylpolysiloxane, cyclopolysiloxane and octamethylcyclotetrasiloxane; and rinsing said contacted articles with a rinsing composition comprising 1H,2H/-hexafluorocyclobutane and optionally at least one organic solvent selected from the group consisting of: hydrocarbons consisting of hexane, heptane, isoheptane, octane, isooctane, methylcyclopentane, cyclohexane, methylcyclohexane and toluene; alcohols having 1–6 carbon atoms; esters composed of fatty acids having about 1–5 carbon atoms and lower alcohols having about 1–6 carbon atoms; and ketones represented by the formula R—CO—$R^1$ wherein R and $R^1$ represent straight or branched saturated hydrocarbons having 1–4 carbon atoms.

3. A method for cleaning articles comprising putting the articles to which pollutants are adhered in contact with a composition comprising 1H,2H/-hexafluorocyclobutane and optionally at least one organic solvent selected from the group consisting of: hydrocarbons consisting of hexane, heptane, isoheptane, octane, isooctane, methylcyclopentane, cyclohexane, methylcyclohexane and toluene; alcohols having 1–6 carbon atoms; esters composed of fatty acids having about 1–5 carbon atoms and lower alcohols having about 1–6 carbon atoms; and ketones represented by the formula R—CO—$R^1$ wherein R and $R^1$ represent straight or branched saturated hydrocarbons having 1–4 carbon atoms.

4. A method for drying articles comprising putting the articles to which pollutants are adhered in contact with a composition comprising 1H,2H/-hexafluorocyclobutane and optionally at least one organic solvent selected from the group consisting of: hydrocarbons consisting of hexane, heptane, isoheptane, octane, isooctane, methylcyclopentane, cyclohexane, methylcyclohexane and toluene; alcohols having 1–6 carbon atoms; esters composed of fatty acids having about 1–5 carbon atoms and lower alcohols having about 1–6 carbon atoms; and ketones represented by the formula R—CO—$R^1$ wherein R and $R^1$ represent straight or branched saturated hydrocarbons having 1–4 carbon atoms.

\* \* \* \* \*

UNITED STATES PATENT AND TRADEMARK OFFICE
CERTIFICATE OF CORRECTION

PATENT NO.   : 5,599,783
DATED        : February 4, 1997
INVENTOR(S)  : IDE et al It is certified that error appears in the above-indentified patent and that said Letters Patent is hereby corrected as shown below:

Title page, Item [86] §102(e) Date:, change "May 9, 1994" to --May 9, 1995--.

Title page, Item [30], change "4-222781" to --5-222781--.

Signed and Sealed this

Third Day of June, 1997

Attest:

BRUCE LEHMAN

*Attesting Officer*     *Commissioner of Patents and Trademarks*